United States Patent
Cadieux, Jr.

(10) Patent No.: US 10,082,467 B2
(45) Date of Patent: Sep. 25, 2018

(54) MENTHOL DETECTION ON TOBACCO

(71) Applicant: ALTRIA CLIENT SERVICES LLC, Richmond, VA (US)

(72) Inventor: Edmond J. Cadieux, Jr., Mechanicsville, VA (US)

(73) Assignee: Altria Client Services LLC, Richmond, VA (US)

( * ) Notice: Subject to any disclaimer, the term of this patent is extended or adjusted under 35 U.S.C. 154(b) by 0 days.

(21) Appl. No.: 15/346,492

(22) Filed: Nov. 8, 2016

(65) Prior Publication Data
US 2017/0052120 A1     Feb. 23, 2017

Related U.S. Application Data

(60) Continuation of application No. 14/802,699, filed on Jul. 17, 2015, now Pat. No. 9,488,580, which is a
(Continued)

(51) Int. Cl.
*B03B 1/00*     (2006.01)
*G01N 21/64*    (2006.01)
(Continued)

(52) U.S. Cl.
CPC .......... *G01N 21/6428* (2013.01); *A24B 1/04* (2013.01); *A24B 13/00* (2013.01); *A24B 15/10* (2013.01); *B07C 5/3427* (2013.01); *B07C 5/366* (2013.01); *B65G 27/00* (2013.01); *C10L 1/003* (2013.01); *G01N 21/359* (2013.01); *G01N 21/55* (2013.01); *G01N 21/6486* (2013.01); *G01N 21/84* (2013.01); *G01N 21/85* (2013.01); *G01N 21/94* (2013.01); *G01N 21/95* (2013.01); *B07C 2501/0018* (2013.01); *C10N 2240/56* (2013.01);
(Continued)

(58) Field of Classification Search
CPC ...... G01N 21/6428; A24B 1/04; A24B 13/00; A24B 15/10; B07C 5/3427; B07C 5/366
USPC ............................................. 209/3, 576, 577
See application file for complete search history.

(56) References Cited

U.S. PATENT DOCUMENTS 3,085,581 A *   4/1963   Rosenberg ............. A24B 15/30
                                                        131/275
3,417,241 A    12/1968   Davis
(Continued)

FOREIGN PATENT DOCUMENTS

CA      2837315 A1    11/2012
DE      20320957 U1    7/2005
(Continued)

OTHER PUBLICATIONS

International Search Report of International Application No. PCT/US2014/026556 dated Jul. 28, 2014.
(Continued)

*Primary Examiner* — Terrell Howard Matthews
(74) *Attorney, Agent, or Firm* — Harness, Dickey & Pierce, P.L.C.

(57) ABSTRACT

A method for detecting mentholated tobacco, comprising irradiating tobacco containing menthol and a fluorescent taggant with radiation and observing the tobacco for fluorescence from the taggant. A system and method for detecting and separating mentholated tobacco from non-mentholated tobacco within a product stream is also provided.

22 Claims, 1 Drawing Sheet

Related U.S. Application Data division of application No. 14/495,756, filed on Sep. 24, 2014, now Pat. No. 9,097,688, which is a continuation-in-part of application No. 13/842,512, filed on Mar. 15, 2013, now Pat. No. 9,073,091.

(51) Int. Cl.

| | |
|---|---|
| *A24B 15/10* | (2006.01) |
| *A24B 13/00* | (2006.01) |
| *G01N 21/84* | (2006.01) |
| *A24B 1/04* | (2006.01) |
| *B07C 5/342* | (2006.01) |
| *B07C 5/36* | (2006.01) |
| *C10L 1/00* | (2006.01) |
| *G01N 21/359* | (2014.01) |
| *G01N 21/55* | (2014.01) |
| *G01N 21/85* | (2006.01) |
| *G01N 21/94* | (2006.01) |
| *B65G 27/00* | (2006.01) |
| *G01N 21/95* | (2006.01) |
| *G01N 21/952* | (2006.01) |

(52) U.S. Cl.
CPC ..... *G01N 21/952* (2013.01); *G01N 2021/646* (2013.01); *G01N 2021/6417* (2013.01); *G01N 2021/6439* (2013.01); *G01N 2021/845* (2013.01); *G01N 2021/8411* (2013.01); *G01N 2021/8466* (2013.01); *G01N 2021/8592* (2013.01)

(56) References Cited

U.S. PATENT DOCUMENTS

| | | | |
|---|---|---|---|
| 3,806,727 A | 4/1974 | Leonard et al. | |
| 3,812,349 A | 5/1974 | Gugliotta et al. | |
| 3,880,289 A | 4/1975 | Gray | |
| 3,985,581 A * | 10/1976 | Stachurski | H01M 2/38 204/273 |
| 3,985,582 A | 10/1976 | Onera | |
| RE29,298 E * | 7/1977 | Banks | A24B 15/30 131/300 |
| 4,057,721 A | 11/1977 | deVial et al. | |
| 4,175,996 A | 11/1979 | Battard et al. | |
| 4,445,520 A | 5/1984 | Knight et al. | |
| 4,480,702 A | 11/1984 | Kelly, Jr. | |
| 4,657,144 A * | 4/1987 | Martin | A24B 1/04 131/108 |
| 4,845,374 A | 7/1989 | White et al. | |
| 4,858,465 A | 8/1989 | Molina | |
| 4,971,077 A * | 11/1990 | Dominguez | A24B 15/30 131/108 |
| 5,048,543 A | 9/1991 | Smith | |
| 5,092,349 A | 3/1992 | Smith et al. | |
| 5,134,291 A | 7/1992 | Ruhl, Jr. et al. | |
| 5,265,732 A | 11/1993 | Long | |
| 5,440,919 A | 8/1995 | Cooper | |
| 5,462,176 A | 10/1995 | Hereford et al. | |
| 5,476,108 A * | 12/1995 | Dominguez | A24C 5/3412 131/108 |
| 5,525,516 A | 6/1996 | Krutak et al. | |
| 5,554,408 A | 9/1996 | Cain et al. | |
| 5,554,480 A | 9/1996 | Patel et al. | |
| 5,665,538 A | 9/1997 | Slater et al. | |
| 5,715,843 A | 2/1998 | Hapke et al. | |
| 5,764,874 A | 6/1998 | White | |
| 5,804,447 A | 9/1998 | Albert et al. | |
| 5,807,605 A | 9/1998 | Tingey et al. | |
| 5,846,830 A | 12/1998 | Demello et al. | |
| 5,887,073 A | 3/1999 | Fazzari et al. | |
| 5,974,860 A | 11/1999 | Kuroda et al. | |
| 5,990,197 A | 11/1999 | Escano et al. | |
| 5,998,211 A | 12/1999 | Albert et al. | |
| 6,025,200 A | 2/2000 | Kaish et al. | |
| 6,058,940 A * | 5/2000 | Lane | A24B 15/18 131/297 |
| 6,060,677 A | 5/2000 | Ulrichsen et al. | |
| 6,064,032 A | 5/2000 | Voss et al. | |
| 6,135,386 A | 10/2000 | Garthaffner | |
| 6,149,719 A | 11/2000 | Houle | |
| 6,166,366 A | 12/2000 | Lewis et al. | |
| 6,312,958 B1 | 11/2001 | Meyer et al. | |
| 6,380,547 B1 | 4/2002 | Gonzalez et al. | |
| 6,384,359 B1 | 5/2002 | Belcastro et al. | |
| 6,444,143 B2 | 9/2002 | Bawendi et al. | |
| 6,477,227 B1 | 11/2002 | Kaiser et al. | |
| 6,511,756 B1 | 1/2003 | Obuchi et al. | |
| 6,529,273 B1 | 3/2003 | Norris et al. | |
| 6,633,043 B2 | 10/2003 | Hegazi et al. | |
| 6,734,383 B1 | 5/2004 | Calcoen et al. | |
| 6,771,365 B1 | 8/2004 | Pirani et al. | |
| 6,795,179 B2 | 9/2004 | Kumar | |
| 6,809,819 B1 | 10/2004 | Vinjamoori et al. | |
| 6,830,310 B2 | 12/2004 | Iu et al. | |
| 6,905,538 B2 | 6/2005 | Auslander | |
| 6,914,678 B1 | 7/2005 | Ulrichsen et al. | |
| 6,926,764 B2 | 8/2005 | Bleikolm et al. | |
| 7,124,944 B2 | 10/2006 | Selinfreund et al. | |
| 7,142,296 B2 * | 11/2006 | Cunningham | B01L 3/5085 356/326 |
| 7,153,557 B2 | 12/2006 | Rancien | |
| 7,157,611 B2 | 1/2007 | Banavali et al. | |
| 7,227,148 B2 | 6/2007 | Sato et al. | |
| 7,256,398 B2 | 8/2007 | Ross et al. | |
| 7,319,039 B2 | 1/2008 | Sullivan | |
| 7,378,675 B2 | 5/2008 | Ross et al. | |
| 7,391,035 B2 | 6/2008 | Kong et al. | |
| 7,441,704 B2 | 10/2008 | Ross | |
| 7,488,945 B2 | 2/2009 | Li et al. | |
| 7,538,324 B2 * | 5/2009 | Deevi | G01N 21/3563 250/339.11 |
| 7,705,144 B2 | 4/2010 | Holmes | |
| 7,749,438 B2 | 7/2010 | Zeinali et al. | |
| 7,767,457 B2 | 8/2010 | Mun et al. | |
| 7,768,643 B1 | 8/2010 | Janssens et al. | |
| 7,800,088 B2 | 9/2010 | Ross et al. | |
| 7,812,953 B2 * | 10/2010 | Tai | G01N 21/35 356/419 |
| 7,816,616 B2 | 10/2010 | Kenny et al. | |
| 7,829,162 B2 * | 11/2010 | Eskra | B41M 5/385 400/241 |
| 7,842,896 B1 | 11/2010 | Calcoen et al. | |
| 7,919,325 B2 | 4/2011 | Eastwood et al. | |
| 7,938,124 B2 | 5/2011 | Izumiya et al. | |
| 7,985,590 B2 * | 7/2011 | McNeil | B82Y 15/00 436/58 |
| 8,415,165 B2 | 4/2013 | Liang et al. | |
| 8,641,933 B2 | 2/2014 | Purdy et al. | |
| 8,692,148 B1 | 4/2014 | Sommer, Jr. et al. | |
| 9,006,599 B2 | 4/2015 | Adams et al. | |
| 9,073,091 B2 | 7/2015 | Cadieux et al. | |
| 9,080,987 B2 * | 7/2015 | Faenza | B07C 5/342 |
| 9,097,668 B2 | 8/2015 | Cadieux et al. | |
| 9,244,017 B2 * | 1/2016 | Cadieux, Jr. | G01N 21/88 |
| 9,361,561 B2 | 6/2016 | Bown et al. | |
| 9,546,966 B2 | 1/2017 | Cadieux, Jr. et al. | |
| 9,733,197 B2 | 8/2017 | Cadieux, Jr. et al. | |
| 9,791,407 B2 * | 10/2017 | Urey | G01N 27/447 |
| 2001/0045378 A1 | 11/2001 | Charles et al. | |
| 2002/0074269 A1 | 6/2002 | Hensley et al. | |
| 2002/0094058 A1 | 7/2002 | Kaiser et al. | |
| 2002/0097833 A1 | 7/2002 | Kaiser et al. | |
| 2002/0122878 A1 | 9/2002 | Kems et al. | |
| 2002/0158212 A1 | 10/2002 | French et al. | |
| 2003/0034282 A1 | 2/2003 | Safai | |
| 2003/0036201 A1 | 2/2003 | Nelson et al. | |
| 2003/0058990 A1 | 3/2003 | Kaiser et al. | |
| 2003/0097833 A1 | 5/2003 | Ingram et al. | |
| 2003/0129283 A1 | 7/2003 | Martinez Carballido | |
| 2003/0141459 A1 | 7/2003 | Hegazi et al. | |
| 2003/0183326 A1 | 10/2003 | O'Connor | |

(56) References Cited

U.S. PATENT DOCUMENTS

| | | | |
|---|---|---|---|
| 2003/0194052 A1* | 10/2003 | Price | G01N 23/223 378/45 |
| 2004/0134504 A1* | 7/2004 | Lane | A24B 15/18 131/290 |
| 2005/0031838 A1 | 2/2005 | Lagunowich et al. | |
| 2005/0083720 A1 | 4/2005 | Fukui et al. | |
| 2005/0092336 A1 | 5/2005 | Zielke et al. | |
| 2005/0092408 A1 | 5/2005 | Lauf et al. | |
| 2005/0236015 A1 | 10/2005 | Goel et al. | |
| 2005/0241989 A1 | 11/2005 | Sant et al. | |
| 2005/0276906 A1 | 12/2005 | Metzger | |
| 2006/0016735 A1 | 1/2006 | Ito et al. | |
| 2006/0081503 A1 | 4/2006 | Wegner | |
| 2006/0118741 A1 | 6/2006 | Ross et al. | |
| 2006/0131517 A1 | 6/2006 | Ross et al. | |
| 2006/0131518 A1 | 6/2006 | Ross et al. | |
| 2006/0186348 A1 | 8/2006 | Nguyen et al. | |
| 2006/0246020 A1 | 11/2006 | Cole et al. | |
| 2006/0262318 A1 | 11/2006 | Sullivan | |
| 2006/0291872 A1 | 12/2006 | Mei et al. | |
| 2007/0023715 A1 | 2/2007 | Ross et al. | |
| 2007/0048761 A1 | 3/2007 | Reep et al. | |
| 2007/0084269 A1 | 4/2007 | Quest et al. | |
| 2007/0187617 A1 | 8/2007 | Kong et al. | |
| 2007/0239367 A1 | 10/2007 | Odegard et al. | |
| 2008/0030712 A1 | 2/2008 | Tokhtuev et al. | |
| 2008/0116272 A1 | 5/2008 | Giering et al. | |
| 2008/0121815 A1 | 5/2008 | Agrawal et al. | |
| 2009/0047531 A1 | 2/2009 | Bartley et al. | |
| 2009/0097833 A1 | 4/2009 | Imada | |
| 2009/0104711 A1 | 4/2009 | Sim | |
| 2009/0185182 A1 | 7/2009 | Kim et al. | |
| 2009/0280341 A1 | 11/2009 | Maruichi et al. | |
| 2009/0321623 A1 | 12/2009 | Ross et al. | |
| 2010/0080456 A1 | 4/2010 | Paul et al. | |
| 2010/0219377 A1 | 9/2010 | Ebert | |
| 2010/0224795 A1 | 9/2010 | Cole et al. | |
| 2010/0226861 A1 | 9/2010 | Cole et al. | |
| 2010/0233447 A1 | 9/2010 | Campbell | |
| 2010/0290040 A1 | 11/2010 | Berghmans | |
| 2010/0320371 A1 | 12/2010 | Agrawal et al. | |
| 2011/0141272 A1 | 6/2011 | Uta et al. | |
| 2011/0151576 A1 | 7/2011 | Yajima et al. | |
| 2011/0168915 A1 | 7/2011 | Yajima et al. | |
| 2011/0216190 A1* | 9/2011 | Shimazu | B07C 5/342 348/135 |
| 2012/0104278 A1 | 5/2012 | Downing et al. | |
| 2012/0267287 A1 | 10/2012 | Bailey | |
| 2012/0302474 A1 | 11/2012 | Faenza | |
| 2013/0082173 A1* | 4/2013 | Cadieux, Jr. | G01N 21/88 250/301 |
| 2013/0179090 A1* | 7/2013 | Conroy | G01N 21/643 702/25 |
| 2013/0188170 A1 | 7/2013 | Wilkins | |
| 2013/0320216 A1 | 12/2013 | Aiko et al. | |
| 2013/0320237 A1 | 12/2013 | Cadieux et al. | |
| 2014/0262966 A1 | 9/2014 | Cadieux, Jr. | |
| 2015/0008162 A1* | 1/2015 | Cadieux, Jr. | A24B 15/10 209/3.3 |
| 2015/0048250 A1 | 2/2015 | Cadieux, Jr. et al. | |
| 2015/0290684 A1 | 10/2015 | Cadieux, Jr. | |
| 2015/0315511 A1 | 11/2015 | Faenza | |
| 2015/0323459 A1 | 11/2015 | Cadieux, Jr. | |
| 2016/0108293 A1 | 4/2016 | Cadieux, Jr. et al. | |
| 2016/0131596 A1 | 5/2016 | Cadieux, Jr. et al. | |
| 2016/0131629 A1 | 5/2016 | Cadieux, Jr. et al. | |

FOREIGN PATENT DOCUMENTS

| | | |
|---|---|---|
| DE | 102011007666 A1 | 10/2012 |
| EP | 0146299 A1 | 6/1985 |
| EP | 0223446 A2 | 5/1987 |
| EP | 657028 B1 | 7/1997 |
| EP | 0897762 A2 | 2/1999 |
| EP | 2715320 A2 | 4/2014 |
| GB | 2091416 A | 7/1982 |
| JP | S61290057 A | 12/1986 |
| JP | S6459095 A | 3/1989 |
| JP | H0666728 A | 3/1994 |
| JP | 2002505426 A | 2/2002 |
| JP | 2002513155 A | 5/2002 |
| JP | 2014512185 A | 5/2014 |
| JP | 2014515487 A | 6/2014 |
| WO | 1991017265 A1 | 11/1991 |
| WO | 9800243 A1 | 1/1998 |
| WO | 9957417 | 11/1999 |
| WO | 1999057417 A2 | 11/1999 |
| WO | 2001025747 A2 | 4/2001 |
| WO | 2001025748 A2 | 4/2001 |
| WO | 2001025764 A1 | 4/2001 |
| WO | 2001025766 A1 | 4/2001 |
| WO | 2001025767 A1 | 4/2001 |
| WO | 2001025820 A2 | 4/2001 |
| WO | 2002068945 A1 | 9/2002 |
| WO | 2008049515 A2 | 5/2008 |
| WO | 2010007390 A2 | 1/2010 |
| WO | 2012030988 A1 | 3/2012 |
| WO | 2012050844 A1 | 4/2012 |
| WO | 2012162701 A2 | 11/2012 |
| WO | 2013181286 A1 | 12/2013 |
| WO | 2014168720 A1 | 10/2014 |

OTHER PUBLICATIONS

International Search Report of International Application No. PCT/US2012/039870 dated Jan. 7, 2013.

International Search Report of International Application No. PCT/US2013/043172 dated Jul. 31, 2013.

Victoria B. Rodriguez et al., "Encapsulation and stabilization of indocyanine green within poly (styrene-alt-maleic anhydride) block-poly (styrene) micelles for near-infrared imaging" Journal of Biomedical Optics, SPIE—International Society for Optical Engineering, vol. 13 No. 1, Jan. 30, 2008, p. 14025-1-140025-10; XP002664215.

Foreign Office Action issued in Canadian Application No. 2,837,315 dated May 23, 2017.

International Preliminary Report on Patentability of International Application No. PCT/US2012/039870 dated Nov. 26, 2013.

International Preliminary Report on Patentability of International Application No. PCT/US2013/043172 dated Dec. 2, 2014.

International Preliminary Report on Patentability of International Application No. PCT/US2014/026556 dated Sep. 15, 2015.

International Preliminary Report on Patentability and Written Opinion of International Application No. PCT/US2015/060179 dated May 16, 2017.

International Search Report of International Application No. PCT/US2015/060179 dated Jan. 27, 2016.

\* cited by examiner

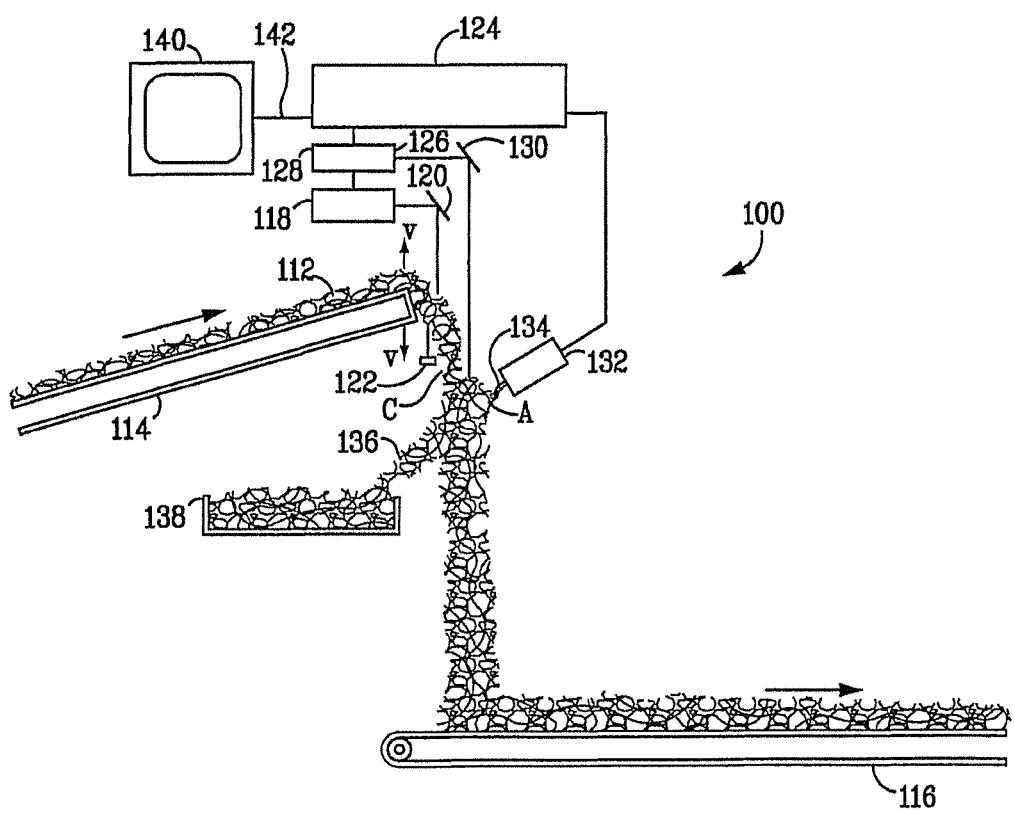

MENTHOL DETECTION ON TOBACCO

RELATED APPLICATION

This patent application is a continuation of co-pending Ser. No. 14/802,699, filed on Jul. 17, 2015, which is a divisional of application Ser. No. 14/495,756, filed on Sep. 24, 2014 (now U.S. Pat. No. 9,097,668), which is a continuation-in-part of application Ser. No. 13/842,512, filed on Mar. 15, 2013 (now U.S. Pat. No. 9,073,091), directed to an ON-LINE OIL AND FOREIGN MATTER DETECTION SYSTEM AND METHOD, the contents of each are hereby incorporated by reference for all that it discloses.

FIELD

This disclosure relates to methods and systems for detecting the presence of a flavorant on an agricultural product used in producing a consumer product. More particularly, this disclosure relates to a method for detecting the presence of menthol on tobacco used to produce smoking articles, and in particular cigarettes and any other smokeable or non-smokeable tobacco products.
Environment Menthol is used as a flavorant in many products including, but not limited to, mentholated cigarettes. Routinely, finished product is "reworked" and reintroduced into raw materials for use in new product. For example, in cigarette manufacturing, cigarettes are routinely diverted from normal production when issues arise in the manufacturing process (e.g. filters not attached correctly, tears in the cigarette paper, etc.). Those cigarettes are sent back to a "ripper room" to recover the tobacco from the cigarette so that it can be reused again. It is very important that mentholated cigarette tobacco not be reintroduced back into non-mentholated product.

It would be advantageous if detection of menthol in tobacco and tobacco products could be conducted on-line, that is in real time during the production process. Heretofore, there has been an absence of an on-line method of detecting menthol on tobacco or in a finished cigarette.

SUMMARY

In one aspect, disclosed herein is a method for detecting mentholated tobacco, comprising irradiating tobacco, especially scrap tobacco, containing menthol and a fluorescent taggant with radiation and observing the scrap tobacco for fluorescence from the taggant, such as wherein the fluorescent taggant is a Stokes shifting taggant, or an anti-Stokes shifting taggant, as previously described.

The process can further comprise separating the mentholated tobacco from non-mentholated tobacco in the scrap.

Alternatively, the process can be conducted when the tobacco is disposed in a tobacco rod which is irradiated with near infrared radiation from a high intensity IR LED light, and reflected IR light is observed using a high speed NIR spectrometer sensor tuned to detect fluorescence emitted from the taggant.

In another aspect, disclosed herein is a composition comprising tobacco, menthol and a fluorescent taggant, such as wherein the fluorescent taggant is a Stokes shifting taggant or an anti-Stokes shifting taggant.

Advantageously, the fluorescent taggant is one which upon pyrolysis decomposes primarily into carbon dioxide and water. Accordingly, the taggant can be an organic taggant, selected from among pyrazolines, oxinates, benzo- xazinones, benzimidazoles, benzthiazoles, thioxanthenes, anthranilic acids, terephthalic acids, aldazines, coumarins, barbituric acids, lumiphores, oxazoles, thiazoles, cumene, stilbenes, and derivatives thereof.

In one form, the organic, fluorescent taggant is one selected from the group consisting of quinine, fluorescein, carmine and indocyanine green and derivatives thereof.

In another form, the fluorescent taggant can be one that absorbs invisible radiation and emits visible radiation, such as one that absorbs ultra violet radiation and emits visible radiation, or one that absorbs infrared radiation and emits visible radiation.

In yet another aspect, disclosed herein is a system for detecting and separating mentholated tobacco from non-mentholated tobacco within a product stream. The system includes: (a) a first conveying means for delivering a product stream; (b) a first detection apparatus for detecting mentholated tobacco, the first detection apparatus positioned proximate the product stream, the first detection apparatus including a high intensity infrared light source directed at the product stream; and a high speed NIR spectrometer sensor tuned to detect a reflected signal from a taggant disposed in the menthol of the mentholated tobacco; and (c) a controller for determining whether the product stream contains mentholated tobacco by monitoring signals obtained from the first detection apparatus.

In one form, the system further includes a second detection apparatus for detecting non-tobacco related material, the second detection apparatus positioned proximate the product stream, the second detection apparatus including a light source for illuminating the product stream and a detector for detecting light reflected from the product stream, wherein the controller also determines whether the product stream contains non-tobacco related material by monitoring signals obtained from the second detection apparatus.

In one form, the system further includes at least one deflecting system responsive to the signals obtained from the first detection apparatus and/or the second detection apparatus, the at least one deflecting system directing fluid under pressure at a portion of the product stream when the controller determines that non-tobacco related material or mentholated tobacco is present in the product stream.

In still yet another aspect, disclosed herein is a method for detecting and separating mentholated tobacco from non-mentholated tobacco within a product stream, the method comprising the steps of: (a) adding a fluorescent taggant to menthol contained in at least one processing machine; (b) conveying a product stream that has been processed by the at least one processing machine; (c) irradiating the conveyed product stream with infrared radiation; (d) detecting infrared radiation emitted from the irradiated product stream due to the presence of the fluorescent taggant and generating a first signal in response thereto; and (e) removing a portion of the conveyed product stream in response to the first signal.

In one form, the method further includes the step of: (f) illuminating the conveyed product stream; (g) detecting light reflected from the illuminated product stream; (h) comparing the light reflected from the illuminated product stream with light that would be expected to be reflected from an illuminated product stream free of non-tobacco related material, and generating a second signal when the reflected light indicates the presence of non-tobacco related material; and (i) removing a portion of the conveyed product stream in response to the second signal.

In one form, the method further includes the step of causing the product stream to fall under the influence of gravity in a cascade.

BRIEF DESCRIPTION OF THE DRAWINGS

The forms disclosed herein are illustrated by way of example, and not by way of limitation, in the FIGURE and in which like reference numerals refer to similar elements and in which:

FIG. 1 presents a schematic representation of a detection and separation system, in accordance herewith.

DETAILED DESCRIPTION

Various aspects will now be described with reference to specific forms selected for purposes of illustration. It will be appreciated that the spirit and scope of the apparatus, system and methods disclosed herein are not limited to the selected forms. Moreover, it is to be noted that the FIGURES provided herein are not drawn to any particular proportion or scale, and that many variations can be made to the illustrated forms.

Each of the following terms written in singular grammatical form: "a," "an," and "the," as used herein, may also refer to, and encompass, a plurality of the stated entity or object, unless otherwise specifically defined or stated herein, or, unless the context clearly dictates otherwise. For example, the phrases "a device," "an assembly," "a mechanism," "a component," and "an element," as used herein, may also refer to, and encompass, a plurality of devices, a plurality of assemblies, a plurality of mechanisms, a plurality of components, and a plurality of elements, respectively.

Each of the following terms: "includes," "including," "has," "having," "comprises," and "comprising," and, their linguistic or grammatical variants, derivatives, and/or conjugates, as used herein, means "including, but not limited to."

Throughout the illustrative description, the examples, and the appended claims, a numerical value of a parameter, feature, object, or dimension, may be stated or described in terms of a numerical range format. It is to be fully understood that the stated numerical range format is provided for illustrating implementation of the forms disclosed herein, and is not to be understood or construed as inflexibly limiting the scope of the forms disclosed herein.

Moreover, for stating or describing a numerical range, the phrase "in a range of between about a first numerical value and about a second numerical value," is considered equivalent to, and means the same as, the phrase "in a range of from about a first numerical value to about a second numerical value," and, thus, the two equivalently meaning phrases may be used interchangeably.

It is to be understood that the various forms disclosed herein are not limited in their application to the details of the order or sequence, and number, of steps or procedures, and sub-steps or sub-procedures, of operation or implementation of forms of the method or to the details of type, composition, construction, arrangement, order and number of the system, system sub-units, devices, assemblies, sub-assemblies, mechanisms, structures, components, elements, and configurations, and, peripheral equipment, utilities, accessories, and materials of forms of the system, set forth in the following illustrative description, accompanying drawings, and examples, unless otherwise specifically stated herein. The apparatus, systems and methods disclosed herein can be practiced or implemented according to various other alternative forms and in various other alternative ways.

It is also to be understood that all technical and scientific words, terms, and/or phrases, used herein throughout the present disclosure have either the identical or similar meaning as commonly understood by one of ordinary skill in the art, unless otherwise specifically defined or stated herein. Phraseology, terminology, and, notation, employed herein throughout the present disclosure are for the purpose of description and should not be regarded as limiting.

Disclosed herein is a method for detecting menthol on tobacco or in finished smoking articles, particularly cigarettes. This method utilizes a taggant that is added to the menthol. An online inspection station can be used to detect the presence of the taggant. The taggant can be detected very reliably in smaller quantities and at higher speeds than detection of menthol without a taggant. Alternatively, mentholated tobacco can be detected visually.

The taggant is comprised of a material that fluoresces at a particular wavelength of light when excited by light, such as for example by ultraviolet light, infrared light or laser light. The wavelengths of light for excitation and emission are dependent on the type of taggant used.

In one form, the fluorescent taggant is a Stokes shifting taggant or an anti-Stokes shifting taggant.

A Stokes shifting taggant is one which absorbs radiation, such as light, at one wavelength and fluoresces/emits radiation at a different wavelength. Conventionally, a Stokes shifting taggant will absorb radiation at a given wavelength and fluoresce or reemit the radiation at lower energy/longer wavelengths. An anti-Stokes shifting taggant absorbs radiation at a given wavelength and remits radiation of higher energy/shorter wavelengths.

In one form of the present invention, the fluorescent taggant absorbs invisible radiation and emits visible radiation. For example, the fluorescent taggant can be one that absorbs ultra-violet radiation and emits visible radiation, or one that absorbs infrared radiation and emits visible radiation.

Alternatively, the fluorescent taggant can be one which absorbs invisible radiation at a first wavelength and emits invisible radiation at a second, different wavelength.

Importantly, the fluorescent taggant should be one which upon pyrolysis decomposes primarily into carbon dioxide and water. Accordingly, the fluorescent taggant is an organic taggant, such as one selected from the group consisting of pyrazolines, oxinates, benzoxazinones, benzimidazoles, benzthiazoles, thioxanthenes, anthranilic acids, terephthalic acids, aldazines, coumarins, barbituric acids, lumiphores, oxazoles, thiazoles, cumene, stilbenes, and derivatives thereof. Advantageously, the organic, fluorescent taggant can be selected from the group consisting of quinine, fluorescein, carmine and indocyanine green and derivatives thereof.

The on-line detection method utilizes a high-speed sensor that is tuned to detect the fluorescent taggant which is added to the menthol. The taggant can be added to the menthol prior to being added to the tobacco product. Accordingly, when combined the product is a composition comprising tobacco, menthol and a fluorescent taggant.

The high-speed sensor consists of a laser diode that is used to excite the taggant at its "excitation" frequency. The detector has a sensor that is tuned to receive light at the taggants "emission" frequency. If the sensor detects the presence of the taggant it will change the state of its output contacts. These output contacts can be used to stop the manufacturing equipment, set an alarm, and divert the suspect product from the normal production flow.

In one form, the detection system utilizes near-infrared (NIR) reflectance, wherein a high intensity IR LED light is directed at tobacco products and reflected IR light is gathered and analyzed using a high speed NIR spectrometer sensor tuned to detect the reflected signal from the taggant added to the tobacco. NIR light can penetrate into various materials, such as tobacco rods, to a depth of several centimeters, even enabling inspection of finished cigarettes. The high speed NIR sensor can detect the taggant, and therefore menthol in finished cigarettes at a rate of 15,000 per minute, or even at a rate of 20,000 per minute.

The fluorescent taggant can be added to menthol solutions so as to provide taggant concentrations on tobacco of between about 10 and 100 ppm, typically at a concentration of about 50 ppm, based on the weight of the tobacco.

The NIR reflectance detectors can be placed virtually anywhere along the process, such that a signal received by a detector at a known location will indicate the presence of the taggant in the processed material almost immediately, readily indicating the presence of menthol in the product.

In another form, the present invention is directed to a method for detecting mentholated tobacco, comprising irradiating scrap tobacco containing menthol and a fluorescent taggant with radiation and observing the scrap tobacco for fluorescence from the taggant.

According to this form, rather than utilizing a high speed detection system incorporating sensors, the fluorescence of the taggant is detected visually by an observer/inspector by irradiating the scrap tobacco with a light which emits wavelengths incorporating those of the absorbance wavelength of the taggant. Accordingly, in this form it is advantageous to select a fluorescent taggant which emits light at visible wavelengths.

Thus, a fluorescent taggant is selected from those described above which absorbs invisible radiation and emits visible radiation. For example, the fluorescent taggant can be one that absorbs ultra-violet radiation and emits visible radiation, or one that absorbs infrared radiation and emits visible radiation. Of course, under certain circumstances it can be suitable to select a taggant which absorbs visible light at a first visible wavelength and emits visible light at a second visible wavelength.

Upon detection of mentholated tobacco product, the process further comprises separating the mentholated tobacco from non-mentholated tobacco in the scrap.

In another aspect, an online system for detecting and separating mentholated tobacco and non-tobacco related material (NTRM) from non-mentholated tobacco is provided. Referring now to FIG. 1, one form of a detection and separation system 100, as disclosed herein, is shown schematically. In operation, a product stream, such as a tobacco stream, 112 containing non-tobacco related material, such as foil, cellophane, and paper, and/or mentholated tobacco, is delivered from a processing line by conveyor 114. Conveyor 114 is preferably a vibrating inclined conveyor which vibrates as shown by arrows V. In one form, conveyor 114 ends above another conveyor 116, which can be an ordinary conveyor belt, and is spaced vertically above conveyor 114 a sufficient distance to accommodate the remainder of the system described below. As product stream 112 reaches the end of conveyor 114, it drops under the influence of gravity in a cascade C to conveyor 116. In one form, because conveyor 114 is inclined, the product stream does not have as great a horizontal velocity when it falls, so that cascade C does not have any significant front-to-back horizontal spread.

Light or electromagnetic radiation having a first wavelength is provided by an optical scanner 118 and is directed toward the cascade C material in the product stream 112 by the mirror 120. Light or electromagnetic radiation that is reflected, refracted or converted by fluorescent or other emission is returned to the mirror 120, and to the optical scanner 118. Some of the light that is not returned interacts with the background element 122, where a portion is returned to the mirror 120, and to the optical scanner 118. These portions returned to the mirror 120 form first, second and third signals.

Light or electromagnetic radiation that is returned from material in the product stream 112 having a wavelength that is longer than the first wavelength is converted into a first signal by the optical scanner 118. Light or electromagnetic radiation having the first wavelength that is reflected by material in the product stream 112 and from the background element 122 is converted into a second signal by the optical scanner 118. Light or electromagnetic radiation having the first wavelength that is scattered by material in the product stream 112 and from the background element 122 is converted into a third signal by the optical scanner 118.

Then, the first, second, and third signals are transformed into a first, second, and third data streams representing the time varying magnitude of each of the signals, and represent the fluorescence channel, reflectance channel, and scatter channel respectively. The data streams are presented to processor 124 and processed.

To detect the presence of mentholated tobacco in the product stream 112, cascade C is irradiated with IR radiation from IR source 126, which may, as shown, be directed toward the cascade C material in product stream 112 by mirror 130. Radiation emitted by mentholated tobacco in cascade C of the product stream 112 is returned to the mirror 130, and then to IR detection device 128. As shown in FIG. 1, the source of radiation 126 and the IR detection device 128 may be housed in one unit, although separate units are within the scope of this disclosure. Likewise, other configurations and orientations for irradiating and detecting radiation, with and without mirrors are also contemplated.

In one form, cascade C of the product stream 112 is irradiated with IR radiation at a wavelength of about 805 nm, and instantaneously emits IR radiation at wavelengths at or about 840 nm from any tagged mentholated tobacco which might be contained in product stream. The emitted IR radiation is in turn detected by IR detection device 128, which sends a signal to processor 124 and is processed.

In one form optical detector 118 has a matrix of electro-optical detectors (not shown), which may be a line-scan camera having a lens and a suitable filter, a photomultiplier tube receiver, or other suitable device.

When optical detector 118 detects non-tobacco related material, or when IR detection device 128 detects mentholated tobacco in product stream 112, processor 124 sends a signal to ejector manifold 132, which is positioned in downstream relation to the region illuminated or radiated by optical detector 118 and irradiated by IR detection device 128. Ejector manifold 132 is in fluid transmission relation to the trajectory of the product stream 112. The ejector manifold 132 includes a plurality of ejector nozzles 134, which are individually directed and controlled to selectively remove undesirable product material 136 from the product stream 112. The ejector nozzles 134 act as conduits for directing fluid pulses to dislodge or otherwise re-direct product material traveling in the trajectory. Individual ejector nozzles 134 contained in the ejector manifold 132 are driven by a plurality of removal signals, which may be provided by processor 124.

Ejector nozzles 134 are connected to a source of high pressure fluid which is preferably air at approximately 80 psi, although other gases, such as steam, or liquids, such as water, can be used. When one of ejector nozzles 134 opens in response to a signal, a blast of air A is directed against that portion of cascade C in which the non-tobacco related material or mentholated tobacco was detected to force that portion 136 of the product stream and/or non-tobacco related material to fall into receptacle 138 for manual sorting, if necessary. In the case of non-mentholated tobacco, it may be returned to the product processing line upstream or downstream of system 100, depending on whether or not rescanning is desired. Alternatively, portion 136 could be deflected to a conveyor that removes it to another area for processing.

As may be appreciated, system 100 allows tobacco to be processed at greater rates than a system in which the tobacco is scanned on a belt conveyor. This is because when product is optically scanned on a belt, it has to be in a "monolayer," or single layer of particles, for all of the particles on the belt to be visible to the optical detector 118. However, as the tobacco or other material falls in cascade C, relative vertical motion between the various particles of tobacco and non-tobacco related material is induced by the turbulence of the falling stream, so there is a greater probability that a particular piece of non-tobacco related material will be visible to optical detector 118 at some point in its fall. Relative vertical motion also results if the non-tobacco related material is significantly lighter or heavier than tobacco so that it has greater or less air resistance as it falls. Relative vertical motion is enhanced by the vibration of conveyor 114 which brings lighter material to the surface of the tobacco before it falls in cascade C, making the lighter material, which is usually non-tobacco related material, easier to detect, as in a monolayer.

The inclination of conveyor 114, in reducing the horizontal spread of cascade C as discussed above, also enhances relative vertical motion because the particles in cascade C have little or no horizontal velocity component. Any horizontal velocity component that a particle has when it falls off conveyor 114 is small because conveyor 114 is inclined, and air resistance quickly reduces the horizontal motion to near zero. The relative vertical motion allows a relatively thicker layer of tobacco or other material to be scanned, so that a greater volume can be scanned per unit of scanning area. Given a constant rate of area scanned per unit time, the increased volume scanned per unit area translates into a higher volume of tobacco or other material scanned per unit time.

In one form, system 100, is provided with a user interface 140 that enables an operator (not shown) to observe and control various operational aspects of the system 100. The user interface 140 may include a CRT or LCD panel for output display. For input, the user interface 140 may include a keyboard, touch-screen or other input means known in the art. The operator can view representations of the articles in the product stream 112 as they are processed in system 100 on the user interface 140. Yet further, the user interface 140 provides a means for the operator to configure the operation of system 100 to make a determination between acceptable product and undesirable product. Data gathered by the user interface 140 and provided to the user interface are transported as user interface data 142.

Suitable optics and control circuitry for use with optical detector 118 are disclosed in U.S. Pat. No. 4,657,144, the contents of which are incorporated herein by reference. Other optics and control circuitry are contemplated for use herein and are within the scope of the instant disclosure.

In operation, non-tobacco related material is detected by comparing its reflectivity, which depends on a combination of color and surface properties, at a given wavelength to a reference level set above the known reflectivity of tobacco at that wavelength, so that even a particle of non-tobacco related material of the same color as tobacco will be detected if its reflectivity is higher than that of tobacco. The optical detector 118 is sensitive to light with a wavelength in the range of from about 200 nm to about 1300 nm. The sensitivity of optical detector 118 to a particular non-tobacco related material or group of non-tobacco related materials can be enhanced by using filters and windows which transmit those wavelengths that are preferentially reflected by the non-tobacco related materials as compared to the tobacco and which absorb all other wavelengths. The effect of this is to greatly reduce the noise in the electronic signal from the detector.

As may be appreciated, when there is no concern that NTRM may comprise a part of the tobacco stream being processed, the system of FIG. 1 may be modified to exclude the components required to detect NTRM. In this form, components including optical detector 118, mirror 120 and background element 122 may be eliminated from system 100.

All or a portion of the methods, systems and subsystems of the exemplary forms can be conveniently implemented using one or more general purpose computer systems, microprocessors, digital signal processors, microcontrollers, and the like, programmed according to the teachings of the exemplary forms disclosed herein, as will be appreciated by those skilled in the computer and software arts.

Appropriate software can be readily prepared by programmers of ordinary skill based on the teachings of the exemplary forms, as will be appreciated by those skilled in the software art. Further, the devices and subsystems of the exemplary forms can be implemented on the World Wide Web. In addition, the devices and subsystems of the exemplary forms can be implemented by the preparation of application-specific integrated circuits or by interconnecting an appropriate network of conventional component circuits, as will be appreciated by those skilled in the electrical art(s). Thus, the exemplary forms are not limited to any specific combination of hardware circuitry and/or software.

Stored on any one or on a combination of computer readable media, the exemplary forms disclosed herein can include software for controlling the devices and subsystems of the exemplary forms, for driving the devices and subsystems of the exemplary forms, for enabling the devices and subsystems of the exemplary forms to interact with a human user, and the like. Such software can include, but is not limited to, device drivers, firmware, operating systems, development tools, applications software, and the like. Such computer readable media further can include the computer program product of a form disclosed herein for performing all or a portion (if processing is distributed) of the processing performed in implementing the methods disclosed herein. Computer code devices of the exemplary forms disclosed herein can include any suitable interpretable or executable code mechanism, including but not limited to scripts, interpretable programs, dynamic link libraries (DLLs), Java classes and applets, complete executable programs, Common Object Request Broker Architecture (CORBA) objects, and the like. Moreover, parts of the processing of the exemplary forms disclosed herein can be distributed for better performance, reliability, cost, and the like.

As stated above, the methods, systems, and subsystems of the exemplary forms can include computer readable medium or memories for holding instructions programmed according to the forms disclosed herein and for holding data structures, tables, records, and/or other data described herein. Computer readable medium can include any suitable medium that participates in providing instructions to a processor for execution. Such a medium can take many forms, including but not limited to, non-volatile media, volatile media, transmission media, and the like. Non-volatile media can include, for example, optical or magnetic disks, magneto-optical disks, and the like. Volatile media can include dynamic memories, and the like. Transmission media can include coaxial cables, copper wire, fiber optics, and the like. Transmission media also can take the form of acoustic, optical, electromagnetic waves, and the like, such as those generated during radio frequency (RF) communications, infrared (IR) data communications, and the like. Common forms of computer-readable media can include, for example, a floppy disk, a flexible disk, hard disk, magnetic tape, any other suitable magnetic medium, a CD-ROM, CDRW, DVD, any other suitable optical medium, punch cards, paper tape, optical mark sheets, any other suitable physical medium with patterns of holes or other optically recognizable indicia, a RAM, a PROM, an EPROM, a FLASH-EPROM, any other suitable memory chip or cartridge, a carrier wave or any other suitable medium from which a computer can read.

The forms disclosed herein, as illustratively described and exemplified hereinabove, have several beneficial and advantageous aspects, characteristics, and features. The forms disclosed herein successfully address and overcome shortcomings and limitations, and widen the scope, of currently known teachings with respect to detecting mentholated tobacco.

In the event that any patents, patent applications, or other references are incorporated by reference herein and define a term in a manner or are otherwise inconsistent with either the non-incorporated portion of the present disclosure or with any of the other incorporated references, the non-incorporated portion of the present disclosure shall control, and the term or incorporated disclosure therein shall only control with respect to the reference in which the term is defined and/or the incorporated disclosure was originally present.

As used herein the terms "adapted" and "configured" mean that the element, component, or other subject matter is designed and/or intended to perform a given function. Thus, the use of the terms "adapted" and "configured" should not be construed to mean that a given element, component, or other subject matter is simply "capable of" performing a given function but that the element, component, and/or other subject matter is specifically selected, created, implemented, utilized, programmed, and/or designed for the purpose of performing the function. It is also within the scope of the present disclosure that elements, components, and/or other recited subject matter that is recited as being adapted to perform a particular function may additionally or alternatively be described as being configured to perform that function, and vice versa.

Illustrative, non-exclusive examples of apparatus and methods according to the present disclosure are presented in the following enumerated paragraphs. It is within the scope of the present disclosure that an individual step of a method recited herein, including in the following enumerated paragraphs, may additionally or alternatively be referred to as a "step for" performing the recited action.

PCT1. A method for detecting mentholated tobacco, comprising irradiating tobacco containing menthol and a fluorescent taggant with radiation and observing the tobacco for fluorescence from the taggant.

PCT2. The method of paragraph PCT1, wherein the fluorescent taggant is a Stokes shifting taggant.

PCT3. The method of paragraph PCT1, wherein the fluorescent taggant is an anti-Stokes shifting taggant.

PCT4. The method of any of paragraphs PCT1-PCT3, wherein the fluorescent taggant is one which upon pyrolysis decomposes primarily into carbon dioxide and water.

PCT5. The method of any of paragraphs PCT1-PCT4, wherein the fluorescent taggant is an organic taggant.

PCT6. The method of paragraph PCT5, wherein the organic taggant is one selected from the group consisting of pyrazolines, oxinates, benzoxazinones, benzimidazoles, benzthiazoles, thioxanthenes, anthranilic acids, terephthalic acids, aldazines, coumarins, barbituric acids, lumiphores, oxazoles, thiazoles, cumene, stilbenes, and derivatives thereof.

PCT7. The method of paragraph PCT5, wherein the organic, fluorescent taggant is selected from the group consisting of quinine, fluorescein, carmine and indocyanine green and derivatives thereof.

PCT8. The method of any of paragraphs PCT1-PCT7, wherein the tobacco is scrap tobacco and further comprising separating the mentholated tobacco from non-mentholated tobacco in the scrap.

PCT9. The method of any of paragraphs PCT1-PCT8, wherein the tobacco is disposed in a tobacco rod which is irradiated with near infrared radiation from a high intensity IR LED light, and reflected IR light is observed using a high speed NIR spectrometer sensor tuned to detect fluorescence emitted from the taggant.

PCT10. A composition comprising tobacco, menthol and a fluorescent taggant.

PCT11. The composition of paragraph PCT10, wherein the fluorescent taggant is a Stokes shifting taggant or an anti-Stokes shifting taggant.

PCT12. The composition of paragraph PCT11 or PCT 12, wherein the fluorescent taggant is one which upon pyrolysis decomposes primarily into carbon dioxide and water.

PCT 13. A system for detecting and separating mentholated tobacco from non-mentholated tobacco within a product stream, comprising: (a) a first conveying means for delivering a product stream; (b) a first detection apparatus for detecting mentholated tobacco, the first detection apparatus positioned proximate the product stream, the first detection apparatus including a high intensity infrared light source directed at the product stream; and a high speed NIR spectrometer sensor tuned to detect a reflected signal from a taggant disposed in the menthol of the mentholated tobacco; and (c) a controller for determining whether the product stream contains mentholated tobacco by monitoring signals obtained from the first detection apparatus.

PCT14. The system of paragraph PCT13, further comprising a second detection apparatus for detecting non-tobacco related material, the second detection apparatus positioned proximate the product stream, the second detection apparatus including a light source for illuminating the product stream and a detector for detecting light reflected from the product stream, wherein the controller also determines whether the product stream contains non-tobacco related material by monitoring signals obtained from the second detection apparatus.

PCT15. The system of paragraph PCT14, further comprising at least one deflecting system responsive to the signals obtained from the first detection apparatus and/or the second detection apparatus, the at least one deflecting system directing fluid under pressure at a portion of the product stream when the controller determines that non-tobacco related material or mentholated tobacco is present in the product stream.

PCT16. The system of paragraph PCT14 or PCT 15, wherein the fluid so directed is effective to remove the non-tobacco related material or mentholated tobacco.

PCT17. The system of any of paragraphs PCT13-PCT16, wherein the taggant is a fluorescent Stokes-shifting taggant, which absorbs radiation at a first wavelength and emits radiation at a second wavelength, different from the first wavelength.

PCT18. A method for detecting and separating mentholated tobacco from non-mentholated tobacco within a product stream, the method comprising the steps of: (a) adding a fluorescent taggant to menthol contained in at least one processing machine; (b) conveying a product stream that has been processed by the at least one processing machine; (c) irradiating the conveyed product stream with infrared radiation; (d) detecting infrared radiation emitted from the irradiated product stream due to the presence of the fluorescent taggant and generating a first signal in response thereto; and (e) removing a portion of the conveyed product stream in response to the first signal.

PCT19. The method of paragraph PCT18, further including the steps of (e) illuminating the conveyed product stream; (f) detecting light reflected from the illuminated product stream; (g) comparing the light reflected from the illuminated product stream with light that would be expected to be reflected from an illuminated product stream free of non-tobacco related material, and generating a second signal when the reflected light indicates the presence of non-tobacco related material; and (h) removing a portion of the conveyed product stream in response to the second signal.

PCT20. The method of paragraph PCT19, further including the step of causing the product stream to fall under the influence of gravity in a cascade.

INDUSTRIAL APPLICABILITY

The containers and processes disclosed herein are applicable to the consumer products industry.

It is believed that the disclosure set forth above encompasses multiple distinct inventions with independent utility. While each of these inventions has been disclosed in its preferred form, the specific forms thereof as disclosed and illustrated herein are not to be considered in a limiting sense as numerous variations are possible. The subject matter of the inventions includes all novel and non-obvious combinations and subcombinations of the various elements, features, functions and/or properties disclosed herein. Similarly, where the claims recite "a" or "a first" element or the equivalent thereof, such claims should be understood to include incorporation of one or more such elements, neither requiring nor excluding two or more such elements.

It is believed that the following claims particularly point out certain combinations and subcombinations that are directed to one of the disclosed inventions and are novel and non-obvious. Inventions embodied in other combinations and subcombinations of features, functions, elements and/or properties may be claimed through amendment of the present claims or presentation of new claims in this or a related application. Such amended or new claims, whether they are directed to a different invention or directed to the same invention, whether different, broader, narrower, or equal in scope to the original claims, are also regarded as included within the subject matter of the inventions of the present disclosure.

What is claimed is:

1. A system for detecting and separating mentholated tobacco from non-mentholated tobacco within a product stream, comprising:
   (a) a first conveying means for delivering a product stream;
   (b) a first detection apparatus for detecting mentholated tobacco, the first detection apparatus positioned proximate the product stream, the first detection apparatus including a high intensity infrared light source directed at the product stream, and a high speed NIR spectrometer sensor tuned to receive light at a taggants emission frequency and detect an emitted signal from a taggant disposed in the menthol of the mentholated tobacco; and
   (c) a controller for determining whether the product stream contains mentholated tobacco by monitoring signals obtained from the first detection apparatus.

2. The system of claim 1, further comprising a second detection apparatus for detecting non-tobacco related material, the second detection apparatus positioned proximate the product stream, the second detection apparatus including a light source for illuminating the product stream and a detector for detecting light emitted from the product stream, wherein the controller also determines whether the product stream contains non-tobacco related material by monitoring signals obtained from the second detection apparatus.

3. The system of claim 2, further comprising at least one deflecting system responsive to the signals obtained from the first detection apparatus and/or the second detection apparatus, the at least one deflecting system directing fluid under pressure at a portion of the product stream when the controller determines that non-tobacco related material or mentholated tobacco is present in the product stream.

4. The system of claim 3, wherein the fluid so directed is effective to remove the non-tobacco related material or mentholated tobacco.

5. The system of claim 4, further comprising a second conveying means located below and spaced vertically from the first conveying means for further conveying the product stream from the first conveying means, wherein the product stream is transferred from the first conveying means to the second conveying means by falling therebetween under the influence of gravity in a cascade.

6. The system of claim 5, wherein the cascade is a turbulent cascade.

7. The system of claim 2, wherein the first conveying means is an inclined vibrating conveyor.

8. The system of claim 2, wherein the fluid is a gas.

9. The system of claim 8, wherein the gas is air.

10. The system of claim 1, wherein the taggant is a fluorescent Stokes-shifting taggant, which absorbs radiation at a first wavelength and emits radiation at a second wavelength, different from the first wavelength.

11. The system of claim 1, wherein the fluorescent taggant is an anti-Stokes shifting taggant.

12. The system of claim 1, wherein the fluorescent taggant is one which upon pyrolysis decomposes primarily into carbon dioxide and water.

13. The system of claim 12, wherein the fluorescent taggant is an organic taggant.

14. The system of claim 13, wherein the organic taggant is one selected from the group consisting of pyrazolines, oxinates, benzoxazinones, benzimidazoles, benzthiazoles, thioxanthenes, anthranilic acids, terephthalic acids, aldazines, coumarins, barbituric acids, lumiphores, oxazoles, thiazoles, cumene, stilbenes, and derivatives thereof.

15. The system of claim 13, wherein the organic, fluorescent taggant is selected from the group consisting of quinine, fluorescein, carmine and indocyanine green and derivatives thereof.

16. A system for detecting mentholated tobacco, comprising a detection apparatus having an infrared light source and a high speed NIR spectrometer sensor positioned proximate a mentholated tobacco stream, wherein the NIR spectrometer sensor is tuned to detect a signal emitted from a taggant disposed in the menthol of the mentholated tobacco.

17. The system of claim 16, wherein the taggant is a fluorescent Stokes-shifting taggant, which absorbs radiation at a first wavelength and emits radiation at a second wavelength, different from the first wavelength.

18. The system of claim 16, wherein the fluorescent taggant is an anti-Stokes shifting taggant.

19. The system of claim 16, wherein the fluorescent taggant is one which upon pyrolysis decomposes primarily into carbon dioxide and water.

20. The system of claim 19, wherein the fluorescent taggant is an organic taggant.

21. The system of claim 20, wherein the organic taggant is one selected from the group consisting of pyrazolines, oxinates, benzoxazinones, benzimidazoles, benzthiazoles, thioxanthenes, anthranilic acids, terephthalic acids, aldazines, coumarins, barbituric acids, lumiphores, oxazoles, thiazoles, cumene, stilbenes, and derivatives thereof.

22. The system of claim 20, wherein the organic, fluorescent taggant is selected from the group consisting of quinine, fluorescein, carmine and indocyanine green and derivatives thereof.

* * * * *